(12) United States Patent
Obata et al.

(10) Patent No.: US 11,311,412 B2
(45) Date of Patent: Apr. 26, 2022

(54) ADHESIVE SHEET FOR COOLING

(71) Applicant: KAO CORPORATION, Chuo-ku (JP)

(72) Inventors: Yosuke Obata, Nerima-ku (JP); Takashi Kodate, Wakayama (JP)

(73) Assignee: KAO CORPORATION, Chuo-ku (JP)

( * ) Notice: Subject to any disclaimer, the term of this patent is extended or adjusted under 35 U.S.C. 154(b) by 1106 days.

(21) Appl. No.: 15/320,413

(22) PCT Filed: Jun. 30, 2014

(86) PCT No.: PCT/JP2014/067405
§ 371 (c)(1),
(2) Date: Dec. 20, 2016

(87) PCT Pub. No.: WO2016/001978
PCT Pub. Date: Jan. 7, 2016

(65) Prior Publication Data
US 2017/0156924 A1    Jun. 8, 2017

(51) Int. Cl.
*A61F 7/02* (2006.01)
*A61F 7/10* (2006.01)
*A61F 7/00* (2006.01)

(52) U.S. Cl.
CPC ............ *A61F 7/02* (2013.01); *A61F 7/10* (2013.01); *A61F 2007/0052* (2013.01);
(Continued)

(58) Field of Classification Search
CPC ...... A61F 7/02; A61F 7/10; A61F 2007/0219; A61F 2007/0214; A61F 2007/0206;
(Continued)

(56) References Cited

U.S. PATENT DOCUMENTS 6,666,836 B1 * 12/2003 Islava .................. A61F 7/02
602/2
2002/0042641 A1 * 4/2002 Johnson ................ A61F 7/02
607/114
(Continued)

FOREIGN PATENT DOCUMENTS

AU    2009246128 B2    4/2015
CN       1571655 A    1/2005
(Continued)

OTHER PUBLICATIONS

Extending European Search Report dated Jan. 31, 2018 in Patent Application No. 14896810.0, 8 pages.
(Continued)

*Primary Examiner* — Kaitlyn E Smith
*Assistant Examiner* — Yasamin Ekrami
(74) *Attorney, Agent, or Firm* — Oblon, McClelland, Maier & Neustadt, L.L.P.

(57) ABSTRACT

The present invention relates to an adhesive sheet for cooling which preferably maintains a cooling effect utilizing the heat of vaporization of water and can exert a persistent high cooling effect.
The adhesive sheet for cooling a hydrous polymer gel (A) and a fiber sheet (B) laminated thereon:
  the hydrous polymer gel (A) having a moisture content of 65% by mass or more and 95% by mass or less,
  the fiber sheet (B) having a thickness of 0.001 mm or more and 1 mm or less, a basis weight of 3 g/m² or more and 70 g/m² or less, and a water absorbency test value of from 1 to 16,000 seconds;
  wherein the adhesive sheet has an amount of moisture of 585 g/m² or more and 1,700 g/m² or less.

13 Claims, 2 Drawing Sheets

(52) U.S. Cl.
CPC .................. *A61F 2007/0203* (2013.01); *A61F 2007/0206* (2013.01); *A61F 2007/0214* (2013.01); *A61F 2007/0219* (2013.01)

(58) Field of Classification Search
CPC ...... A61F 2007/0203; A61F 2007/0052; A61F 2007/0244; A61F 2007/0223; A61K 9/7023
See application file for complete search history.

(56) References Cited

U.S. PATENT DOCUMENTS

| | | | | |
|---|---|---|---|---|
| 2002/0081321 | A1* | 6/2002 | Konno | A61K 8/0208 424/401 |
| 2004/0156886 | A1 | 8/2004 | Kose | |
| 2004/0197502 | A1 | 10/2004 | Usui et al. | |
| 2006/0058860 | A1* | 3/2006 | Ferdinand | A61F 7/10 607/108 |
| 2007/0083249 | A1* | 4/2007 | Tu | A61F 7/00 607/108 |
| 2007/0098769 | A1* | 5/2007 | Champion | A61K 31/57 424/448 |
| 2008/0041543 | A1* | 2/2008 | Dyer | A61K 8/0208 162/111 |
| 2009/0088825 | A1* | 4/2009 | Ota | A61F 7/02 607/96 |
| 2011/0034887 | A1* | 2/2011 | Forden | D06M 13/148 604/291 |
| 2012/0157904 | A1* | 6/2012 | Stein | A61F 7/02 602/43 |
| 2015/0335471 | A1* | 11/2015 | Nakashima | A61K 47/22 607/112 |

FOREIGN PATENT DOCUMENTS

| | | |
|---|---|---|
| CN | 2848220 Y | 12/2006 |
| CN | 101252898 A | 8/2008 |
| CN | 201150591 Y | 11/2008 |
| CN | 202568582 U | 12/2012 |
| CN | 202751688 U | 2/2013 |
| CN | 202875581 U | 4/2013 |
| CN | 102772590 B | 3/2014 |
| JP | 2001-104359 A | 4/2001 |
| JP | 2001104359 A * | 4/2001 |
| JP | 2004-33279 A | 2/2004 |
| JP | 2007-29606 A | 2/2007 |
| JP | 2007-191812 A | 8/2007 |
| JP | 2009-201549 A | 9/2009 |
| JP | 2012-237073 A | 12/2012 |
| JP | 2013-59602 A | 4/2013 |
| JP | 2013-132409 A | 7/2013 |
| JP | 2013132409 A * | 7/2013 |
| JP | 2014-100250 A | 6/2014 |
| JP | 2015-123083 A | 7/2015 |
| JP | 2015-124146 A | 7/2015 |
| JP | 2016-124870 A | 7/2016 |
| JP | 2017-25020 A | 2/2017 |
| JP | 2017-226609 A | 12/2017 |
| WO | 02/100384 A1 | 12/2002 |

OTHER PUBLICATIONS

Hajime Goto, et al., "Transition of Anti-Inflammatory Analgesic Poultice for External Use", Kagaku Kogaku, vol. 76, No. 9, Total 5 Pages, (2012), (with Partial English Translation).

Akira Hinata, et al., "Kinousei fushokufu—Genryou Kaihatsu Kara Sangyo Riyou Made (Functional Non-woven fabric—From Development of Raw Materials to Industrial Application-)", CMC Publishing Co., Ltd., Total 4 Pages, (2004), (with Partial English Translation).

Hensel, et al., "Thermoreception and temperature regulation", Academic Press, Total 14 Pages, (1981).

International Search Report dated Sep. 9, 2014 in PCT/JP14/067405 Filed Jun. 30, 2014.

* cited by examiner

ADHESIVE SHEET FOR COOLING

FIELD OF THE INVENTION

The present invention relates to adhesive sheets for cooling.

BACKGROUND OF THE INVENTION

Cooling gel sheets including non-woven fabric and a hydrous polymer gel layer laminated have been conventionally known. The cooling gel sheet is known to exert a local cooling effect utilizing the heat of vaporization of water when the sheet is attached to the skin and used with the hydrous polymer gel layer side in contact with the skin. Such a cooling gel sheet is composed of a thick fiber layer of non-woven or woven fabric having a basis weight of about 100 g/m² and a hydrous gel layer containing polyacrylic acid or a polyacrylic acid derivative as the base material. Attempts have been made to increase the water content of the gel in order to improve the cooling performance and increase the thickness of the hydrous gel layer in order to increase the persistent cooling (for example, Non Patent Literatures 1 and 2).

Various improvements have been made on these cooling gel sheets in recent years. For example, Patent Literature 1 discloses a patch including a hydrous adhesive layer and a fiber sheet layer composed of hydrophobic fiber having a specific mass per unit area and thickness laminated with the aim of improving the cooling effect while reducing stickiness upon use. Additionally, Patent Literature 2 discloses a sheet patch including a sheet support prepared by mixing rayon and pulp and having a specific mass per unit area and an adhesive layer, in which the tensile shear adhesion strength on superposed adhesion of the support surface and the adhesive surface is adjusted to a specific range to thereby prevent delamination of the superposed portion upon use and additionally to provide cooling action.

Meanwhile, it is known that a cool feeling caused when a cooling sheet is attached to the skin becomes easier to sense as a change in the skin temperature per elapsed time becomes greater (Non Patent Literature 3). Thus, when the skin temperature of the sheet-attached area is increased or when the skin temperature is kept the same for a predetermined time, the cool feeling may be very likely to be impaired.

[Patent Literature 1] JP-A-2004-33279
[Patent Literature 2] International Publication No. WO 2002/100384
[Non Patent Literature 1] Hajime Goto et al., "Kagaku Kogaku", vol. 76, No. 9, 2012
[Non Patent Literature 2] Akira Hinata et al., "Kinousei fushokufu—Genryou Kaihatsu Kara Sangyo Riyou Made (Functional Non-woven fabric—From Development of Raw Materials to Industrial Application—)", CMC Publishing Co., Ltd., 2004
[Non-Patent Literature 3] Hensel et al., "Thermoreception and temperature regulation", Academic Press, 1981

SUMMARY OF THE INVENTION

The present invention relates to an adhesive sheet for cooling comprising a hydrous polymer gel (A) and a fiber sheet (B) laminated thereon:

the hydrous polymer gel (A) having a moisture content of 65% by mass or more and 95% by mass or less, and the fiber sheet (B) having a thickness of 0.001 mm or more and 1 mm or less, a basis weight of 3 g/m² or more and 70 g/m² or less, and a water absorbency test value of 1 to 16,000 seconds;

wherein the adhesive sheet has an amount of moisture of 585 g/m² or more and 1700 g/m² or less.

Amid development of these various cooling gel sheets, there is a need for providing a cooling gel sheet which can provide not only a temporary cooling effect but also a persistent cooling effect. However, in the patch described in Patent Literature 1 above, the hydrophobic fiber cannot sufficiently absorb moisture in the hydrous gel layer. Thus, water vaporizes insufficiently, and the cooling effect obtained from the heat of vaporization tends to be reduced. The sheet patch described in Patent Literature 2 above is also still in need of improvement to sufficiently enhance the cooling effect.

The present inventors thus made extensive investigations to solve the aforementioned problems, as a result, found that by employing both a fiber sheet having a certain thickness and basis weight and having a water absorbency test value within a certain range and a hydrous polymer gel having a high moisture content laminated thereon to provide an adhesive sheet for cooling retaining a large amount of moisture as a whole, thus obtained sheet greatly facilitates transfer of moisture from the gel to the fiber sheet and transpiration of moisture from the fiber sheet to thereby decrease the temperature of the sheet-attached area persistently, and provide a preferable cool feeling for a long period, and the present invention has been completed.

According to the present invention, a large amount of moisture contained in the hydrous polymer gel is preferably transferred to the fiber sheet as well as being transpired from the fiber sheet efficiently and persistently. This enables the heat of vaporization of water to be effectively utilized for a long period and a preferable cool feeling to be persistent. Accordingly, the sheet can exert a high cooling effect in a high-temperature and humid environment, in which the heat of vaporization of the moisture tends to be decreased and the cooling effect tends to be reduced. According to the present invention, an excessive amount of moisture is prevented from residing in the fiber sheet, and thus, a preferable feeling of use is imparted while a comfortable cool feeling is maintained.

DETAILED DESCRIPTION OF THE INVENTION

The present invention will now be described in detail.

The adhesive sheet for cooling of the present invention comprises a hydrous polymer gel (A) having a moisture content within a certain range and a fiber sheet (B) having a basis weight, thickness, and water absorbency within a certain range described below laminated thereon, wherein the entire adhesive sheet has an amount of moisture within a certain range. Upon use, the surface on the side of the hydrous polymer gel of the adhesive sheet for cooling is intended to be attached to an object. When the adhesive sheet for cooling of the present invention is attached to the skin, the heat is transmitted from the skin to the hydrous polymer gel (A), and at the same time, the moisture in the hydrous polymer gel is transferred to the fiber sheet (B). Thus, the moisture is transpired from the fiber sheet (B), and the heat supplied from the skin is removed by utilizing the heat of vaporization of water. As the result, the sheet-attached area undergoes cooling. Meanwhile, to the fiber sheet (B) laminated on the hydrous polymer gel (A), the moisture is persistently transferred at an appropriate rate from the hydrous polymer gel (A), as described later. This improves the persistence of moisture transpiration from the fiber sheet (B), enabling a cool feeling to persist for a long period.

The moisture content in the hydrous polymer gel (A) constituting the adhesive sheet for cooling of the present invention is 65% by mass or more, preferably 66% by mass or more, more preferably 68% by mass or more, still more preferably 70% by mass or more, from the viewpoint of persistently cooling the sheet-attached area by utilizing the heat of vaporization of water. The moisture content in the hydrous polymer gel (A) constituting the adhesive sheet for cooling of the present invention is 95% by mass or less, preferably 93% by mass or less, still more preferably 92% by mass or less, from the similar viewpoint. The moisture content in the hydrous polymer gel constituting the adhesive sheet for cooling of the present invention is also from 65 to 95% by mass, preferably from 66 to 93% by mass, more preferably from 68 to 92% by mass, still more preferably from 70 to 92% by mass. Such an amount of water that achieves the moisture content should be blended in a gel stock solution.

Incidentally, the moisture content of the hydrous polymer gel (A) may be measured by using a moisture meter utilizing the Carl-Fischer method (for example, Hiranuma moisture measurement apparatus AQV-300 series).

The amount of the hydrous polymer gel (A) laminated is preferably 615 $g/m^2$ or more, more preferably 650 $g/m^2$ or more, still more preferably 670 $g/m^2$ or more, even more preferably 700 $g/m^2$ or more, from the viewpoints of continuously transferring a sufficient amount of moisture to the fiber sheet in combination with the action caused by a fiber sheet described below and of avoiding accumulation of heat when the sheet is attached to the skin. The amount of the hydrous polymer gel (A) laminated is preferably 2,600 $g/m^2$ or less, more preferably 2,200 $g/m^2$ or less, still more preferably 2,000 $g/m^2$ less, even more preferably 1,400 $g/m^2$ or less, from the similar viewpoints. The amount of the hydrous polymer gel (A) laminated is also preferably from 615 to 2,600 $g/m^2$, more preferably from 650 to 2,200 $g/m^2$, still more preferably from 670 to 2,000 $g/m^2$, even more preferably from 700 to 1,400 $g/m^2$. Incidentally, the amount of the hydrous polymer gel (A) laminated means an amount in the form of the stock solution.

The polymer forming the hydrous polymer gel (A) may be any polymer which may retain water to thereby form gel having appropriate elasticity and flexibility. Examples of the polymer include those having a functional group of carboxyl group, a sulfuric acid group, or a phosphoric acid group. Specific examples of the polymer include carboxy vinyl polymers, polyacrylic acid and its salts, poly(meth)acrylic acid or its salts such as acrylic acid-alkyl methacrylate copolymers; anionic cellulose derivatives such as carboxymethyl cellulose or its salts and carboxyethyl cellulose or its salts; gellan gum, pectin, xanthan gum, carrageenan, agar, alginic acid and its salts, and anionic starch derivatives.

One or more of these polymers can be used. Of these, one or more members selected from the group consisting of poly(meth)acrylic acid or its salts, anionic cellulose derivatives, and carrageenan are preferred, one or two members selected from the group consisting of polyacrylic acid or its salts and carboxymethyl cellulose or its salts are more preferred, and carboxymethyl cellulose or its salts are still more preferred, from the viewpoints of combining a high water-holding capacity, sufficient gel strength, and flexibility to follow the irregularity and movement of the skin and of being capable of providing a larger amount of moisture to the fiber sheet (B). The content of these polymers in the hydrous polymer gel (A) is preferably 0.1% by mass or more, more preferably 0.5% by mass or more, still more preferably 1% by mass or more, from the viewpoint of continuously transferring a sufficient amount of moisture to the fiber sheet (B) described below in combination with the action caused by the fiber sheet (B). The content of these polymers is preferably 30% by mass or less, more preferably 20% by mass or less, still more preferably 15% by mass or less, even more preferably 12% by mass or less, from the similar viewpoint. The content of these polymers in the hydrous polymer gel (A) is also preferably from 0.1 to 30% by mass, more preferably from 0.5 to 20% by mass, still more preferably from 1 to 15% by mass, even more preferably from 1 to 12% by mass. Such an amount of the polymers that achieves the polymer content should be blended in the stock solution of the hydrous polymer gel.

On forming the hydrous polymer gel (A) from the polymers described above, a crosslinking agent should be additionally used and allowed to react with the functional groups of the polymers. Examples of the crosslinking agent include one or more members selected from the group consisting of oxides, hydroxides, or salts containing ions of metal such as aluminum, magnesium, titanium, chromium, manganese, iron, cobalt, nickel, zinc, cadmium, lead, calcium, and potassium; cationic polymers such as polyamino acid, for example, polylysine; and polyfunctional epoxy compounds such as ethylene glycol diglycidyl ether, polyethylene glycol diglycidyl ether, glycerin diglycidyl ether, and glycerin triglycidyl ether.

The hydrous polymer gel (A) described above preferably contains a cooling agent as required, from the viewpoint of imparting a further cooler feeling. This can further enhance the cool feeling. This makes the adhesive sheet for cooling of the present invention suitable to be used, for example, in scenes where a cooler feeling may be desired in a hot and humid environment as in summer.

The cooling agent may be any agent which provides a cool feeling and a refreshing feeling, and specific examples thereof include 1-menthol, d-menthol, dl-menthol, cineol, menthane diol, menthyl lactate, 1-menthyl glyceryl ether, menthyl ethylamino oxalate, menthyl pyrrolidone carboxylate, menthyl succinate, menthyl glutarate, ethyl menthane carboxamide, menthane carbonyl glycine ethyl ester, menthone, menthone glycerin acetal, 2-sec-butylcyclohexanone, isopulegol, pulegol, N,2,3-trimethyl-2-isopropylbutanamide, thymol, eugenol, anethole, methyl salicylate, camphor, spilanthol, trimethylcyclohexanol, and 3-1-menthoxy-2-methylpropan-1,2-diol. Essential oils containing the substance above may be also used, and examples thereof include mentha oil, peppermint oil, spearmint oil, eucalyptus oil, sassafras oil, and wintergreen oil. These may be used singly, or two or more of them may be used in combination. Of these, from the viewpoints of suppressing skin irritation and of providing a preferable smell, one or more members selected from the group consisting of 1-menthol, menthyl lactate, 1-menthyl glyceryl ether, menthyl ethylamino oxalate, menthane carbonyl glycine ethyl ester, isopulegol, and camphor are preferred, one or more members selected from the group consisting of 1-menthol, menthyl lactate, menthyl ethylamino oxalate, and camphor are more preferred, and one or two members selected from the group consisting of 1-menthol and menthyl lactate are still more preferred.

The content of the cooling agent is preferably 0.0001% by mass or more, more preferably 0.001% by mass or more, still more preferably 0.005% by mass or more in the hydrous polymer gel (A), from the viewpoint of allowing a cool feeling to further persist, and preferably 10% by mass or less, more preferably 5% by mass or less, still more preferably 1% by mass or less from the viewpoint of suppressing irritation. Such an amount of the cooling agent that achieves the content should be blended in the stock solution of the hydrous polymer gel, and the cooling agent may substantially not be contained. The content of cooling agent is also preferably from 0.0001 to 10% by mass, more preferably from 0.001 to 5% by mass, still more preferably from 0.005 to 1% by mass in the hydrous polymer gel (A). The adhesive sheet for cooling of the present invention persistently reduce the temperature of a sheet-attached area to persistently provide a preferable cool feeling, and thus, can sufficiently continue to realize a cool feeling even if containing a small amount of the cooling agent or containing substantially no cooling agent.

The hydrous polymer gel (A) preferably has a pH of from 3.5 to 7. The pH of normal human skin usually falls within the range above described. Since excessive variation in the skin pH may interferes with the functions of the skin, it is preferred that the hydrous polymer gel, which comes in direct contact with the skin, have a pH in the range above described. The pH may be adjusted by use of a pH adjusting agent as appropriate. Examples of the pH adjusting agent suitably used include organic acids such as succinic acid, citric acid, and tartaric acid or their salts, or phosphoric acid or its salts. The hydrous polymer gel (A) has a pH of more preferably from 4 to 7, still more preferably from 4 to 6.5.

Incidentally, the pH of the hydrous polymer gel (A) is a value obtained by mixing and stirring 0.5 g of the hydrous polymer gel in 4.5 g of pure water until dissolution is completed and measuring the pH of the dispersion with a pH meter (B-212, HORIBA).

The hydrous polymer gel (A) may contain, in addition to the above components, other components usually used in cosmetics and pharmaceuticals, for example, a moisturizing agent; an oily agent; a surfactant such as an anionic surfactant, a cationic surfactant, amphoteric surfactant, and a nonionic surfactant; a medicinal ingredient; a preservative; an antioxidant; an ultraviolet absorber; a solubilizing agent; a colorant; a fragrance other than cooling agent described in literatures such as "Gousei kouryo: kagaku to shouhin chishiki (Synthetic fragrances: Chemistry and product knowledge)", written by Motoichi Indo, 1996, published by The Chemical Daily Co., Ltd.; "Perfume and Flavor Chemicals", written by STEFFEN ARCTAMDER, 1969 and the like, as appropriate. Of these components, a polyhydric alcohol such as glycerin, diglycerin, polyglycerin, propylene glycol, dipropylene glycol, 1,3-butylene glycol, and polyethylene glycol is preferably contained as a moisturizing agent. These components also may be contained in the fiber sheet (B).

In order to produce the hydrous polymer gel (A), hydrous polymer gel stock solution is prepared first which contains a polymer, water, and, as required, a cooling agent and other components. Then, the hydrous polymer gel stock solution is sandwiched between peelable films and spread using a Baker type applicator or the like. At this time, as one of the surfaces sandwiching the gel stock solution, a fiber sheet may be used. Subsequently the gel is aged at room temperature or under warming at 35 to 60° C. for several hours to several days to thereby provide a hydrous polymer gel W. Incidentally, the hydrous polymer gel (A) can be produced not only by the above production method, but also in accordance with a conventionally known method.

Examples of methods for laminating the hydrous polymer gel (A) and the fiber sheet (B) include the above described method in which the fiber sheet (B) is used as one of the surfaces sandwiching the above gel stock solution, a method in which, after application of the gel stock solution on a peelable film, a fiber sheet is overlapped or pressed and laminated on the gel, and a method in which, after the hydrous polymer gel (A) is once prepared, the hydrous polymer gel (A) is applied or pressed and laminated on the fiber sheet (B). Alternatively, the sheet may take a form in which the hydrous polymer gel (A) obtained is attached to the skin followed by covering with the fiber sheet (B).

The fiber sheet (B) constituting the adhesive sheet for cooling of the present invention preferably contains a water absorbent fiber. Specific examples of the water absorbent fiber include water absorbent fibers such as rayon, cotton, cupra, linen, wool, silk, acetate, cellulose, wood pulp, and non-wood pulp; polymers having a hydrophilic group such as a hydroxyl group, a carboxyl group, a sulfonic acid group, an amido group, and an amino acid group, water absorbent fibers composed of a hydrophilic polymer, for example, polyvinyl alcohol, polyethylene glycol, cellulose acetate, polyacrylamide, melamine resin, nylon, and hydrophilic polyurethane; water absorbent fibers composed of a hydrophilized hydrophobic polymer such as hydrophilized polyester; and composite fibers containing a hydrophobic portion composed of a hydrophobic polymer such as polyethylene and polypropylene and a water absorbent portion. These may be used singly, or two or more of them may be used in combination. Examples of the composite fiber include fibers having a core-sheath structure composed of a core portion and a sheath portion. Such fibers also may have a porous structure which contains voids holding moisture inside the fiber.

Incidentally, at least part of respective strings of the water absorbent fiber may be oriented in one direction in the fiber sheet (B) or may be oriented in random directions.

Preferable exemplary form of the fiber sheet (B) used in the present invention include non-woven fabric, woven fabric, knitted fabric, or paper containing these fibers, from the viewpoint that transfer of moisture from the hydrous polymer gel to the fiber sheet (B) and moisture transpiration from the fiber sheet (B) are extremely preferably facilitated. Of these, fiber sheets containing one or more water absorbent fibers selected from the group consisting of rayon, cotton, cupra, cellulose, pulp, and polyvinyl alcohol, or mixed fiber sheets containing such water absorbent fiber and hydrophobic fiber are more preferred. Especially, fiber sheets containing one or more water absorbent fibers selected from the group consisting of rayon, cellulose, pulp, and polyvinyl alcohol, or mixed fiber sheets containing such a water absorbent fiber and a hydrophobic fiber are still more preferred.

The content of the water absorbent fiber in the fiber sheet (B) is preferably 1% by mass or more, more preferably 5% by mass or more, still more preferably 10% by mass or more, from the viewpoint that transfer of moisture from the hydrous polymer gel (A) to the fiber of the fiber sheet (B) and moisture transpiration from the fiber are extremely preferably facilitated. The content of the water absorbent fiber in the fiber sheet (B) is preferably 100% by mass or less. The content of the water absorbent fiber in the fiber sheet (B) is also preferably from 1 to 100% by mass, more preferably from 5 to 100% by mass, still more preferably from 10 to 100% by mass.

The basis weight of the fiber sheet (B) in the present invention is 3 g/m² or more, and from the viewpoint that transfer of moisture from the hydrous polymer gel (A) to the fiber of the fiber sheet (B) and moisture transpiration from the fiber are extremely preferably facilitated, preferably 5 g/m² or more, more preferably 10 g/m² or more, still more preferably 14 g/m² or more. The basis weight of the fiber sheet (B) in the present invention is 70 g/m² or less, and from the similar viewpoint, preferably 60 g/m² or less, more preferably 50 g/m² or less, still more preferably 40 g/m² or less. The basis weight of the fiber sheet (B) in the present invention is also from 3 to 70 g/m², preferably from 5 to 60 g/m², more preferably from 10 to 50 g/m², still more preferably from 14 to 40 g/m².

The fiber density of the fiber sheet (B) is preferably from 30,000 to 1,000,000 g/m³, more preferably from 50,000 to 800,000 g/m³, still more preferably from 60,000 to 500,000 g/m³, from the viewpoints that transfer of moisture from the hydrous polymer gel (A) to the fiber sheet (B) and moisture transpiration from the fiber sheet (B) are extremely preferably facilitated and that the cooling performance is improved in the adhesive sheet for cooling of the present invention.

The thickness of the fiber sheet (B) is 0.001 mm or more, preferably 0.005 mm or more, more preferably 0.01 mm or more, still more preferably 0.02 mm or more, from the viewpoints that transpiration of the moisture contained in the hydrous polymer gel (A) is not prevented and that this effect is allowed to persist for a long period. The thickness of the fiber sheet (B) is 1 mm or less, preferably 0.8 mm or less, more preferably 0.7 mm or less, still more preferably 0.6 mm or less, from the similar viewpoints. The thickness of the fiber sheet is also from 0.001 to 1 mm, preferably from 0.005 to 0.8 mm, more preferably from 0.01 to 0.7 mm, still more preferably from 0.02 to 0.6 mm.

The thickness of the fiber sheet (B) is a value measured using a constant pressure thickness gauge (PG-11 J-type manufactured by TECLOCK Corporation (measuring force 3.7 g/cm², gauge head diameter 10 cm²).

The fiber sheet (B) is a fiber sheet which exhibits a water absorbency test value calculated from the following test of from 1 to 16,000 seconds. Incidentally, the water absorbency test value in the present invention is a value obtained by placing a 5×5 cm fiber sheet piece on a cylinder having a diameter of 4 cm, dropping a droplet (about 0.04 mL) of water from a height of 1 cm above the fiber sheet, and measuring the time (seconds) required from when the water droplet reaches the fiber sheet piece to when the specular reflection of water eliminates. When a portion or all of the water permeated from the surface opposite to the side on which the water was dropped immediately after water was dropped, it was assumed that no water absorbency test value was obtained. The measurement environment was 25° C. and 40±5% RH. Incidentally, a context that a portion or all of the water permeated from the surface opposite to the side on which the water was dropped means, as referred herein, that the dropped water is present as a water droplet on the surface opposite to the side on which the water was dropped.

The above water absorbency test is a method in compliance with JIS L1907 (Dropping Method) Testing methods for water absorbency of textiles, Byreck Method. A fiber sheet (B) having a value obtained by the water absorbency test of 16,000 seconds or less can preferably absorb moisture from the hydrous polymer gel and persistently transpire moisture from the surface opposite to the side of the fiber sheet in contact with the hydrous polymer gel, and thus can sufficiently exert a cooling effect over a long period. Alternatively, a fiber sheet having a water absorbency test value of 1 second or more can avoid excess water absorption from the hydrous polymer gel (A), and thus can reduce the amount of moisture which resides in the fiber sheet (B) without transpiring. The fiber sheet (B) can not only effectively reduce a stickiness feeling of the fiber sheet (B) upon use but also further facilitate persistent moisture transpiration from the surface of the fiber sheet (B).

The water absorbency test value is from 1 to 16,000 seconds, and from the viewpoint described above, preferably from 1 to 14,000 seconds, more preferably from 1 to 12,000 seconds.

The fiber sheet (B) has a value, obtained by multiplying the water absorbency test value to the one-third power by the fiber density, of preferably from $0.25 \times 10^6$ to $2.2 \times 10^6$ seconds$^{1/3}$·g/m³, more preferably from $0.5 \times 10^6$ to $2.1 \times 10^6$ seconds$^{1/3}$·g/m³, still more preferably from $0.8 \times 10^6$ to $2 \times 10^6$ seconds$^{1/3}$·g/m³, from the viewpoints that transfer of moisture from the hydrous polymer gel (A) to the fiber sheet (B) and moisture transpiration from the fiber sheet (B) are extremely preferably facilitated and that the cooling performance is improved in the adhesive sheet for cooling of the present invention. Incidentally, it is believed that the value obtained by multiplying the water absorbency test value to the one-third power by the fiber density means the diffusion rate of water in the fiber sheet (B).

The amount of moisture in the adhesive sheet for cooling of the present invention is 585 g/m² or more, preferably 600 g/m² or more, more preferably 650 g/m² or more from the viewpoint of persistently cooling a sheet-attached area by utilizing the heat of vaporization of water. The amount of moisture of the adhesive sheet for cooling of the present invention is 1700 g/m² or less, preferably 1,600 g/m² or less, more preferably 1,500 g/m² or less, still more preferably 1,250 g/m² or less from the viewpoint of cooling performance.

Incidentally, the amount of moisture of the adhesive sheet for cooling of the present invention means an amount of moisture upon use after production of the adhesive sheet for cooling of the present invention, and is a value obtained by multiplying the amount of the hydrous polymer gel stock solution laminated (g/m²) by the moisture content in the hydrous polymer gel stock solution.

In the adhesive sheet for cooling of the present invention, the mass ratio of the moisture to the fiber in the adhesive sheet for cooling (moisture mass/fiber mass in the adhesive sheet for cooling) is preferably 9 or more, more preferably 15 or more, still more preferably 20 or more, even more preferably 25 or more, from the viewpoints that transfer of moisture from the hydrous polymer gel (A) to the fiber sheet (B) and moisture transpiration from the fiber sheet (B) are extremely preferably facilitated and that the cooling performance is improved in the adhesive sheet for cooling of the present invention. In the adhesive sheet for cooling of the present invention, the mass ratio of the moisture to the fiber in adhesive sheet for cooling (moisture mass/fiber mass of the adhesive sheet for cooling) is preferably 320 or less, more preferably 150 or less, still more preferably 100 or less, even more preferably 70 or less, from the viewpoint of cooling performance and persistent cooling. In the adhesive sheet for cooling of the present invention, the mass ratio of the moisture to the fiber in adhesive sheet for cooling (moisture mass/fiber mass of the adhesive sheet for cooling) is also preferably from 9 to 320, more preferably from 15 to 150, still more preferably from 20 to 100, even more preferably from 25 to 70.

The adhesive sheet for cooling of the present invention can cool the skin effectively and persistently when the side of the hydrous polymer gel (A) opposite to the side in contact with the fiber sheet (B) is attached to the skin. The sheet finds wide applications as, for example, cosmetics, pharmaceuticals, quasi-pharmaceutical products, and general merchandise to be attached to the outer skin (including scalp). More specifically, the sheet can be used by attaching it to the skin of a desired area, for example, when cooling of the forehead or the bottom of the neck is desired in case of acute fever, or when cooling of the limbs, body, neck, face, or head is desired before bedtime on hot and sleepless summer nights, and when a cool feeling is desired in the heat hot summer outdoors in a case of hot and humid conditions. Incidentally, hot and humid conditions mean conditions of an ambient temperature of 26° C. or more and 60° C. or less and a relative humidity of 55% or more and 100% or less.

In connection with the aforementioned embodiments, the present invention further discloses the following adhesive sheets for cooling.

[1] An adhesive sheet for cooling comprising a hydrous polymer gel (A) and a fiber sheet (B) laminated thereon, wherein the hydrous polymer gel (A) has a moisture content of 65% by mass or more and 95% by mass or less, wherein the fiber sheet (B) comprises a water absorbent fiber and has a thickness of 0.001 mm or more and 1 mm or less, a basis weight of 3 g/m$^2$ or more and 70 g/m$^2$ or less, and a water absorbency test value of from 1 to 16,000 seconds, and wherein the adhesive sheet has an amount of moisture of 585 g/m$^2$ or more and 1700 g/m$^2$ or less.

[2] The adhesive sheet for cooling according to [1], wherein the moisture content in the hydrous polymer gel (A) is preferably 66% by mass or more, more preferably 68% by mass or more, still more preferably 70% by mass or more, and preferably 93% by mass or less, still more preferably 92% by mass or less.

[3] The adhesive sheet for cooling according to [1] or [2], wherein the amount of the hydrous polymer gel (A) laminated is preferably 615 g/m$^2$ or more, more preferably 650 g/m$^2$ or more, still more preferably 670 g/m$^2$ or more, even more preferably 700 g/m$^2$ or more, and also preferably 2,600 g/m$^2$ or less, more preferably 2,200 g/m$^2$ or less, still more preferably 2,000 g/m$^2$ or less, even more preferably 1,400 g/m$^2$ or less.

[4] The adhesive sheet for cooling according to any one of [1] to [3], wherein the polymer forming the hydrous polymer gel (A) is preferably one or more members selected from the group consisting of poly(meth)acrylic acid or its salts, anionic cellulose derivatives, and carrageenan, more preferably one or two members selected from the group consisting of polyacrylic acid or its salts and carboxymethyl cellulose or its salts, still more preferably carboxymethyl cellulose or a salt.

[5] The adhesive sheet for cooling according to any one of [1] to [4], wherein the hydrous polymer gel (A) preferably further comprises a cooling agent.

[6] The adhesive sheet for cooling according to any one of [1] to [5], wherein the cooling agent is preferably one or more members selected from the group consisting of 1-menthol, menthyl lactate, 1-menthyl glyceryl ether, menthyl ethylamino oxalate, menthane carbonyl glycine ethyl ester, isopulegol, and camphor, more preferably one or more members selected from the group consisting of 1-menthol, menthyl lactate, menthyl ethylamino oxalate, and camphor, still more preferably one or two members selected from the group consisting of 1-menthol and lactate menthyl.

[7] The adhesive sheet for cooling according to any one of [1] to [6], wherein the content of the cooling agent in the hydrous polymer gel is preferably 0.0001% by mass or more, more preferably 0.001% by mass or more, still more preferably 0.005% by mass or more, and also preferably 10% by mass or less, more preferably 5% by mass or less, still more preferably 1% by mass or less.

[8] The adhesive sheet for cooling according to any one of [1] to [7], wherein the hydrous polymer gel (A) has a pH of preferably from 3.5 to 7, more preferably from 4 to 7, still more preferably from 4 to 6.5.

[9] The adhesive sheet for cooling according to any one of [1] to [8], wherein the fiber sheet (B) is preferably in the form of non-woven fabric.

[10] The adhesive sheet for cooling according to any one of [1] to [9], wherein the fiber sheet (B) is a fiber sheet preferably comprising a water absorbent fiber, more preferably a mixed fiber sheet comprising a water absorbent fiber and a hydrophobic fiber.

[11] The adhesive sheet for cooling according to any one of [1] to [10], wherein the fiber sheet (B) preferably comprises one or more water absorbent fibers selected from the group consisting of rayon, cellulose, pulp, and polyvinyl alcohol.

[12] The adhesive sheet for cooling according to any one of [1] to [11], wherein the content of the water absorbent fiber in the fiber sheet (B) is preferably to mass or more, more preferably 5% by mass or more, still more preferably 10% by mass or more.

[13] The adhesive sheet for cooling according to any one of [1] to [12], wherein the basis weight of the fiber sheet (B) is preferably 5 g/m$^2$ or more, more preferably 10 g/m$^2$ or more, still more preferably 14 g/m$^2$ or more, and also preferably 60 g/m$^2$ or less, more preferably 50 g/m$^2$ or less, still more preferably 40 g/m$^2$ or less.

[14] The adhesive sheet for cooling according to any one of [1] to [13], wherein the fiber density of the fiber sheet (B) is preferably from 30,000 to 1,000,000 g/m$^3$, more preferably from 50,000 to 800,000 g/m$^3$, still more preferably from 60,000 to 500,000 g/m$^3$.

[15] The adhesive sheet for cooling according to any one of [1] to [14], wherein the thickness of the fiber sheet (B) is preferably 0.005 mm or more, more preferably 0.01 mm or more, still more preferably 0.02 mm or more, and also preferably 0.8 mm or less, more preferably 0.7 mm or less, still more preferably 0.6 mm or less.

[16] The adhesive sheet for cooling according to any one of [1] to [15], wherein the water absorbency test value of the fiber sheet (B) is preferably from 1 to 14,000 seconds, more preferably from 1 to 12,000 seconds.

[17] The adhesive sheet for cooling according to any one of [1] to [16], wherein the water absorbency test value of the fiber sheet (B) is a value obtained by placing a 5×5 cm fiber sheet piece on a cylinder having a diameter of 4 cm, dropping a droplet of water from a height of 1 cm above the fiber sheet, and measuring the time (seconds) required from when the water droplet reaches the fiber sheet piece to when the specular reflection of water eliminates.

[18] The adhesive sheet for cooling according to any one of [1] to [17], wherein a value obtained by multiplying the water absorbency test value to the one-third power by the fiber density of the fiber sheet (B) is preferably from $0.25 \times 10^6$ to $2.2 \times 10^6$ seconds$^{1/3} \cdot$g/m$^3$, more preferably from $0.5 \times 10^6$ to $2.1 \times 10^6$ seconds$^{1/3} \cdot$g/m$^3$, still more preferably from $0.8 \times 10^6$ to $2 \times 10^6$ seconds$^{1/3} \cdot$g/m$^3$.

[19] The adhesive sheet for cooling according to any one of [1] to [18], wherein the amount of moisture of the adhesive sheet for cooling is preferably 600 g/m$^2$ or more, more preferably 650 g/m$^2$ or more, and also preferably 1,600 g/m$^2$ or less, more preferably 1,500 g/m$^2$ or less, still more preferably 1,250 g/m$^2$ or less.

[20] The adhesive sheet for cooling according to any one of [1] to [19], wherein the mass ratio of the moisture to the fiber in the adhesive sheet for cooling (moisture mass/fiber mass in the adhesive sheet for cooling) is preferably 9 or more, more preferably 15 or more, still more preferably 20 or more, even more preferably 25 or more, and also preferably 320 or less, more preferably 150 or less, still more preferably 100 or less, even more preferably 70 or less.

[21] Use of the adhesive sheet for cooling according to any one of [1] to [20] for use under hot and humid conditions.

[22] Use of the adhesive sheet for cooling according to any one of [1] to [20] for persistently reduce the temperature of a sheet-attached area for at least 15 minutes after the sheet is attached.

[23] The adhesive sheet for cooling according to any one of [1] to [20], wherein the adhesive sheet is used to cool the skin by attaching the side of the hydrous polymer gel (A) opposite to the side in contact with the fiber sheet (B) to the skin.

[24] A method for cooling, wherein the adhesive sheet for cooling according to any one of [1] to [20] is used to persistently reduce the temperature of a sheet-attached area for at least 15 minutes after the sheet is attached.

EXAMPLES

The present invention will be described in more detail based on Examples, but the present invention is not intended to be limited by these Examples.

Test Example 1: Measurement of Water Absorbency Test Value of Fiber Sheet

In accordance with the following method, the water absorbency test value of the fiber sheets of Reference Examples 1 to 13 shown below was measured. Specifically, a 5×5 cm fiber sheet piece was placed on a cylinder having a diameter of 4 cm, a droplet (about 0.04 mL) of water was dropped from a height of 1 cm above the fiber sheet, and the time (seconds) required from when the water droplet reaches the fiber sheet piece to when the specular reflection of water eliminates was measured. Incidentally, if a portion or all of the water permeated from the surface opposite to the side on which the water was dropped when the water droplet was dropped, it was assumed that no water absorbency test value was obtained. The measurement environment was 25° C. and 40±5% RH. The results are shown in Table 1.

Test Example 2: Measurement of Thickness of Fiber Sheet

The thickness of the fiber sheet was measured using a constant pressure thickness gauge (PG-11 J-type manufactured by TECLOCK Corporation (measuring force 3.7 g/cm$^2$, gauge head diameter 10 cm$^2$). The results are shown in Table 1.

TABLE 1

| Reference Example | Fiber composition | Composition ratio | Basis weight (g/m$^2$) | Thickness (mm) | Water absorbency test value: X (seconds) | Fiber density: Y (g$^3$) | $X^{1/3} \cdot Y$ seconds$^{1/3} \cdot$ g/m$^3$ |
|---|---|---|---|---|---|---|---|
| 1 | Rayon | 100 | 18 | 0.06 | 88 | 300000 | 1334388 |
| 2 | Rayon | 100 | 20 | 0.07 | 102 | 285714 | 1334951 |
| 3 | PVA + Rayon + Pulp + PP/PE | 3 + 37 + 32 + 28 | 17 | 0.07 | 133 | 242857 | 1239657 |
| 4 | PVA + Rayon + PP/PE | 10 + 50 + 40 | 21 | 0.14 | 152 | 150000 | 800520 |
| 5 | Cellulose | 100 | 13.5 | 0.07 | 122 | 192857 | 956509 |
| 6 | PET/Low melting point PET + Pulp | 90 + 10 | 20 | 0.28 | 10531 | 71429 | 1565652 |
| 7 | PET/Low melting point PET + Pulp | 80 + 20 | 20 | 0.24 | 10956 | 86957 | 1931314 |
| 8 | PET/Low melting point PET + Pulp | 80 + 20 | 40 | 0.68 | 9231 | 58824 | 1233959 |
| 9 | PET/Low melting point PET + Pulp | 80 + 20 | 50 | 0.85 | 8931 | 58824 | 1220444 |
| 10 | Rayon + Polyolefin | 80 + 20 | 80 | 0.65 | 0.1 | 123077 | 57127 |
| 11 | Pulp | 100 | 40 | 0.70 | 0.5 | 57143 | 45354 |
| 12 | Polyolefin | 100 | 50 | 0.55 | 17335 | 90909 | 2352783 |
| 13 | PET/PE | 100 | 18 | 0.37 | — | 48649 | — |

The raw material species and component ratio of fibers constituting each fiber sheet are shown below.

Reference Examples 1 to 13: Fiber Sheet Layer

Reference Example 1: rayon (basis weight 18 thickness 0.06 mm)

Reference Example 2: rayon (basis weight 20 g/m$^2$, thickness 0.07 mm)

Reference Example 3: polyvinyl alcohol (PVA)+rayon+pulp+(polypropylene (PP) (core portion)/polyethylene (PE) (sheath portion))=3+37+32+28 (% by mass) (basis weight 17 g/m$^2$, thickness 0.07 mm)

Reference Example 4: PVA+rayon+(PP (core portion)/PE (sheath portion))=10+50+40 (% by mass) (basis weight 21 g/m$^2$, thickness 0.14 mm)

Reference Example 5: cellulose (basis weight 13.5 g/m$^2$, thickness 0.07 mm)

Reference Example 6: (polyethylene terephthalate (PET (core portion))/low melting point PET (sheath portion))+pulp=90+10 (% by mass) (basis weight 20 g/m$^2$, thickness 0.28 mm)

Reference Example 7: (PET (core portion)/low melting point PET (sheath portion))+pulp=80+20 (% by mass) (basis weight 20 g/m$^2$, thickness 0.24 mm)

Reference Example 8: (PET (core portion)/low melting point PET (sheath portion))+pulp=80+20 (% by mass) (basis weight 40 g/m$^2$, thickness 0.68 mm)

Reference Example 9: (PET (core portion)/low melting point PET (sheath portion))+pulp=80+20 (% by mass) (basis weight 50 g/m², thickness 0.85 mm)

Reference Example 10: rayon+polyolefin=80+20 (basis weight 80 g/m², thickness 0.65 mm)

Reference Example 11: pulp (basis weight 40 thickness 0.7 mm)

Reference Example 12: polyolefin (basis weight 50 g/m², thickness 0.55 mm)

Reference Example 13: PET (core portion)/PE (sheath portion) (basis weight 18 g/m², thickness 0.37 mm)

From the results of Table 1, it can be seen that the water absorbency test value of each fiber sheet of Reference Examples 1 to 9 represented a value of from 1 to 16,000 seconds and each sheet had a water absorption property in a certain range. In contrast, the fiber sheets as generally used in cooling gel sheet (Reference Examples 10 and 11) conventionally had fast water absorbency. A fiber sheet composed of a hydrophobic fiber and having a basis weight of about 50 g/m² (Reference Example 12) had very slow water absorbency. For a fiber sheet composed of a hydrophobic fiber and having a basis weight as small as 18 g/m² (Reference Example 13), water permeated through the fiber sheet at the moment when a water droplet was dropped. Thus, water absorbency test values of the fiber sheet could not be obtained.

Examples 1 to 9 and Comparative Examples 1 to 5

In accordance with the formulation of hydrous polymer gels shown in Table 2, hydrous polymer gels were prepared. Subsequently, each hydrous polymer gel was laminated on each fiber sheet of Reference Examples 1 to 13 in an amount shown in Table 2 to thereby provide an adhesive sheet for cooling after heat aging.

Specifically, first, a mixture of propylene glycol into which glycerin and methyl paraoxybenzoate were warmed and dissolved, sodium carboxymethyl cellulose, and dried aluminum hydroxide gel was placed into a kneader, then, a succinic acid aqueous solution was added to the mixture to thereby prepare a uncrosslinked gel stock solution. Subsequently, the uncrosslinked gel stock solution obtained was applied on and sandwiched between polypropylene films. The thickness of the gel was adjusted with a Baker type applicator such that the amount of the hydrous polymer gel laminated reached 750 g/m² (amount of moisture: 656 g/m²) on the stock solution basis, thereby providing a sheet. After the sheet obtained was encapsulated and sealed within an aluminum pillow package, the sheet was aged at 50° C. for five days to allow crosslinking reaction in the gel stock solution to proceed thereby forming a hydrous polymer gel. Incidentally, the gel stock solution prepared had a pH of 4.7. The hydrous polymer gel obtained was die-cut into a square (area 25 cm²), from one side of which the polypropylene film was peeled off. Each fiber sheet (5×5 cm) was pressed and laminated onto the hydrous polymer gel to thereby provide an adhesive sheet for cooling. The hydrous polymer gel of the adhesive sheet for cooling obtained had a pH of 5.1.

Subsequently, the cooling effect was measured in accordance with the method in the following Test Example 3 using each adhesive sheet for cooling obtained. The results are shown in Table 2.

Test Example 3: Cooling Effect Measurement

Each adhesive sheet for cooling was attached to a hot plate set at 36° C. to measure the temperature of the hot plate at the sheet-attached area with a thermistor probe. The measurement was conducted in a thermo-hygrostat at 28° C. and 60% RH. With respect to cooling performance, the temperatures before, 10 minutes after, and 30 minutes after the sheet was attached were measured. The plate temperature change $\Delta T_1$ (° C.) was calculated by the following expression to thereby evaluate the cooling effect.

Plate temperature change $\Delta T_1$(° C.)=(Plate temperature 10 or 30 minutes after the sheet was attached)−(Plate temperature before the sheet was attached)

TABLE 2

| | Structure | Example 1 | 2 | 3 | 4 | 5 | 6 | 7 | 8 | 9 | 10 | 11 | 12 |
|---|---|---|---|---|---|---|---|---|---|---|---|---|---|
| Fiber sheet | Reference Example number of Table 1 | 1 | 2 | 3 | 4 | 5 | 6 | 7 | 8 | 9 | 3 | 3 | 7 |
| | Water absorbency test value (seconds) | 88 | 102 | 133 | 152 | 122 | 10531 | 10956 | 9231 | 8931 | 133 | 133 | 10956 |
| | Thickness (mm) | 0.06 | 0.07 | 0.07 | 0.14 | 0.07 | 0.28 | 0.24 | 0.68 | 0.85 | 0.07 | 0.07 | 0.24 |
| | Basis weight (g/m²) | 18 | 20 | 17 | 21 | 13.5 | 20 | 20 | 40 | 50 | 17 | 17 | 20 |
| | (Water absorbency test value)^(1/3) × Fiber density (×10⁶) | 1.33 | 1.33 | 1.24 | 0.80 | 0.96 | 1.57 | 1.93 | 1.23 | 1.22 | 1.24 | 1.24 | 1.93 |
| Hydrous polymer gel layer (% by mass) | Glycerin | 3 | 3 | 3 | 3 | 3 | 3 | 3 | 3 | 3 | 3 | 4 | 20.7 |
| | Propylene glycol | 5 | 5 | 5 | 5 | 5 | 5 | 5 | 5 | 5 | 5 | — | 5 |
| | 1,3-Butylene glycol | — | — | — | — | — | — | — | — | — | — | 3 | — |
| | Sodium lyacrylate | — | — | — | — | — | — | — | — | — | — | 2 | — |
| | Polyscrylia acid | — | — | — | — | — | — | — | — | — | — | 5 | — |
| | Sodium carboxymethyl cellulose | 3.5 | 3.5 | 3.5 | 3.5 | 3.5 | 3.5 | 3.5 | 3.5 | 3.5 | 3.5 | 6 | 3.5 |
| | Dried aluminum hydroxide gel | 0.15 | 0.15 | 0.15 | 0.15 | 0.15 | 0.15 | 0.15 | 0.15 | 0.15 | 0.15 | 0.2 | 0.15 |
| | Succinic acid | 0.4 | 0.4 | 0.4 | 0.4 | 0.4 | 0.4 | 0.4 | 0.4 | 0.4 | 0.4 | 0.3 | 0.4 |
| | Tartaric acid | — | — | — | — | — | — | — | — | — | — | 0.1 | — |
| | Preservative | 0.25 | 0.25 | 0.25 | 0.25 | 0.25 | 0.25 | 0.25 | 0.25 | 0.25 | 0.25 | 0.05 | 0.25 |
| | PEG400 | — | — | — | — | — | — | — | — | — | — | — | — |
| | Frescolat ML | — | — | — | — | — | — | — | — | — | — | — | — |
| | l-Menthol | — | — | — | — | — | — | — | — | — | — | — | — |
| | Fragrance | 0.3 | 0.3 | 0.3 | 0.3 | 0.3 | 0.3 | 0.3 | 0.3 | 0.3 | — | — | — |
| | Purified water | 87.4 | 87.4 | 87.4 | 87.4 | 87.4 | 87.4 | 87.4 | 87.4 | 87.4 | 87.7 | 79.4 | 70 |
| | Total | 100 | 100 | 100 | 100 | 100 | 100 | 100 | 100 | 100 | 100 | 100 | 100 |
| | Amount of hydrous polymer gel laminated (g/m²) | 750 | 750 | 750 | 750 | 750 | 750 | 753 | 750 | 750 | 1500 | 750 | 1312 |
| Adhesive sheet for cooling | Amount of moisture in adhesive sheet produced (g/m²) | 656 | 656 | 656 | 656 | 656 | 656 | 656 | 656 | 656 | 1315 | 595 | 418 |
| | Moisture mass/fiber mass in sheet | 36.4 | 32.8 | 38.6 | 31.2 | 48.6 | 32.8 | 32.8 | 16.4 | 13.1 | 77.4 | 35.0 | 45.9 |
| Cooling effect ($\Delta T_1$ °C.) | After 10 minutes | −3.41 | −3.38 | −3.26 | −3.18 | −2.99 | −3.29 | −3.30 | −2.98 | −2.72 | −3.08 | −2.80 | −3.35 |
| | After 30 minutes | −3.22 | −3.19 | −3.20 | −3.15 | −2.92 | −3.23 | −3.20 | −2.90 | −2.66 | −2.98 | −2.75 | −3.25 |

TABLE 2-continued

| | | Example | | | Comparative Example | | | | | | | |
|---|---|---|---|---|---|---|---|---|---|---|---|---|
| | | 13 | 14 | 15 | 1 | 2 | 3 | 4 | 5 | 6 | 7 | 8 |
| Structure | | | | | | | | | | | | |
| Fiber sheet | Reference Example number of Table 1 | 7 | 3 | 3 | None | 10 | 11 | 12 | 13 | 7 | 7 | 7 |
| | Water absorbency test value (seconds) | 10956 | 133 | 133 | — | 0.1 | 0.5 | 17335 | — | 10956 | 10956 | 10956 |
| | Thickness (mm) | 0.24 | 0.07 | 0.07 | — | 0.65 | 0.70 | 0.55 | 0.37 | 0.24 | 0.24 | 0.24 |
| | Basis weight (g/m²) | 20 | 17 | 17 | — | 80 | 40 | 50 | 18 | 20 | 20 | 20 |
| | (Water absorbency test value)$^{1/3}$ × Fiber density (×10$^6$) | 1.93 | 1.24 | 1.24 | — | 0.06 | 0.05 | 2.35 | — | 1.93 | 1.93 | 1.93 |
| Hydrous polymer gel layer (% by mass) | Glycerin | 3 | 3 | 3 | 3 | 3 | 3 | 3 | 3 | 27.4 | 27.4 | 10.7 |
| | Propylene glycol | 2.2 | 5 | 5 | 5 | 5 | 5 | 5 | 5 | 5 | 5 | 5 |
| | 1,3-Butylene glycol | — | — | — | — | — | — | — | — | — | — | — |
| | Sodium lyacrylate | — | — | — | — | — | — | — | — | — | — | — |
| | Polyscrylia acid | — | — | — | — | — | — | — | — | — | — | — |
| | Sodium carboxymethyl cellulose | 2 | 3.5 | 3.5 | 3.5 | 3.5 | 3.5 | 3.5 | 15 | 3.5 | 3.5 | 4 |
| | Dried aluminum hydroxide gel | 0.15 | 0.15 | 0.15 | 0.15 | 0.15 | 0.15 | 0.15 | 0.15 | 0.15 | 0.15 | 0.15 |
| | Succinic acid | 0.4 | 0.4 | 0.4 | 0.4 | 0.4 | 0.4 | 0.4 | 0.4 | 0.4 | 0.4 | 0.4 |
| | Tartaric acid | — | — | — | — | — | — | — | — | — | — | — |
| | Preservative | 0.25 | 0.25 | 0.25 | 0.25 | 0.25 | 0.25 | 0.25 | 0.25 | 0.25 | 0.25 | 0.25 |
| | PEG400 | — | — | 0.97 | — | — | — | — | — | — | — | — |
| | Frescolat ML | — | 0.9 | — | — | — | — | — | — | — | — | — |
| | l-Menthol | — | 0.1 | 0.03 | — | — | — | — | — | — | — | — |
| | Fragrance | — | 0.3 | 0.3 | 0.3 | 0.3 | 0.3 | 0.3 | 0.3 | 0.3 | 0.3 | 0.3 |
| | Purified water | 92 | 86.4 | 86.4 | 87.4 | 87.4 | 87.4 | 87.4 | 87.4 | 63 | 63 | 79.2 |
| | Total | 100 | 100 | 100 | 100 | 100 | 100 | 100 | 100 | 100 | 100 | 100 |
| Adhesive sheet for cooling | Amount of hydrous polymer gel laminated (g/m²) | 1312 | 750 | 750 | 750 | 750 | 750 | 750 | 750 | 750 | 1050 | 2312 |
| | Amount of moisture in adhesive sheet produced (g/m²) | 1207 | 656 | 655 | 656 | 656 | 656 | 556 | 656 | 472 | 661 | 1831 |
| | Moisture mass/fiber mass in sheet | 60.4 | 38.6 | 38.6 | — | 8.2 | 16.4 | 13.1 | 36.4 | 23.6 | 33.1 | 91.6 |
| Cooling effect (ΔT$_1$ °C) | After 10 minutes | -3.50 | — | — | -2.61 | -2.44 | -2.33 | -2.23 | -2.64 | -3.27 | -2.11 | -1.86 |
| | After 30 minutes | -3.35 | — | — | -2.53 | -2.35 | -2.23 | -2.21 | -2.56 | -2.55 | -2.05 | -1.73 |

According to the results in Table 2, it can be seen that Examples 1 to 9, in which the fiber sheets of Reference Examples 1 to 9 had been used, exhibited a larger plate temperature change than that of Comparative Example 1, in which the sheet had a single layer structure composed singly of a hydrous polymer gel, and that lamination of the fiber layer further enhanced the cooling effect. In contrast, it can be seen that Comparative Examples 2 to 5, in which the fiber sheets of Reference Examples 10 to 13 had been used, had a cooling effect equivalent to or lower than that of Comparative Example 1.

Examples 10 and 11 and Comparative Examples 6 and 7

Hydrous gels formed in accordance with the formulations shown in Table 2 was used. Adhesive sheets for cooling were prepared in the same manner as Example 3 except that, in Example 10, the thickness was adjusted such that the amount of the hydrous polymer gel laminated reached 1,500 g/m$^2$ (amount of moisture: 1,315 g/m$^2$) on the stock solution basis and that, in Examples 11, the moisture content of the hydrous polymer gel was set to 79.4% by mass. Alternatively, in Comparative Example 6, an adhesive sheet for cooling was prepared in the same manner as Example 7 except that the moisture content of the hydrous polymer gel was set to 63% by mass. In Comparative Example 7, an adhesive sheet for cooling was prepared in the same manner as Example 7 except that the moisture content of the hydrous polymer gel was set to 63% by mass and additionally the gel was applied to adjust the thickness such that the amount of the hydrous polymer gel laminated reached 1050 g/m$^2$ (amount of moisture: 661 g/m$^2$) on the stock solution basis.

Subsequently, the cooling effect was measured in accordance with the method in the above Test Example 3 using each adhesive sheet for cooling obtained. The results are shown in Table 2.

According to the results in Table 2, it can be seen that Example 10, in which the fiber sheet of Reference Example 3 had been used and additionally the amount of moisture in the adhesive sheet for cooling was 1,315 g/m$^2$, had a large plate temperature change and a preferable cooling effect. It also can be seen that Example 11, in which the fiber sheet of Reference Example 3 has been used and sodium carboxymethyl cellulose, sodium polyacrylate, and polyacrylic acid had been blended as polymer gel agents, also had a large plate temperature change and a preferable cooling effect. In contrast, it can be seen that Comparative Example 6, in which the amount of moisture in the adhesive sheet for cooling was 472 g/m$^2$, had a preferable cooling effect 10 minutes after the sheet was attached, but the cooling effect was significantly reduced after 30 minutes, and a persistent cooling effect could not be achieved. Additionally, it can be seen that, in Comparative Example 7, in which the amount of moisture of the adhesive sheet for cooling was 585 g/m$^2$ or more, but the moisture content of the hydrous polymer gel was as low as 63% by mass, the cooling effect was weak both 10 and 30 minutes after the sheet was attached.

Examples 12 and 13 and Comparative Example 8

Hydrous polymer gels formed in accordance with the formulations shown in Table 2 was used. Adhesive sheets for cooling were each prepared in the same manner as Example 7 except that, in Example 12, the moisture content of the hydrous polymer gel was set to 70% by mass, that, in Example 13, the moisture content of the hydrous polymer gel was set to 92% by mass and the gel was applied to adjust the thickness such that the amount of the hydrous polymer gel sheet laminated reached 1,312 g/m$^2$ on the stock solution basis, and that, in Comparative Example 8, the moisture content of the hydrous polymer gel was set to 79.2% by mass and the thickness was adjusted such that the hydrous polymer gel sheet laminated reached 2,312 g/m$^2$.

Subsequently, the cooling effect was measured in accordance with the method in the above Test Example 3 using each adhesive sheet for cooling obtained. The results are shown in Table 2.

According to the results in Table 2, it can be seen that, in Example 12, in which the moisture content of the hydrous polymer gel was 70% by mass and Example 13, in which the moisture content was 92% by mass, the plate temperature change was large and the cooling effect was preferable. In contrast, it can be seen that, in Comparative Example 8, in which the moisture content of the hydrous polymer gel was moderately 79.2% by mass but the amount of moisture in the adhesive sheet for cooling was extremely as high as 1,831 g/m$^2$, the cooling effect was inferior.

Test Example 4: Measurement of Cooling Effect on Human Skin

The adhesive sheets for cooling each obtained in Examples 1, 3, 5, and 7 and Comparative Examples 5 and 8 and a commercially available cooling gel sheet were used to measure a cooling effect on human skin. Specifically, subjects were healthy males in their thirties. Under measurement conditions of a temperature of 29° C. and a humidity of 60% RH, a thermistor probe was attached to the forehead in advance to measure the skin surface temperature of the forehead before a sheet was attached. Thereafter, the adhesive sheets for cooling of Examples 1, 3, 5, and 7 and Comparative Examples 5, 8, and 9 were each attached to the skin such that the sheet was superposed on the thermistor probe. The skin surface temperature at time point when a predetermined time passed after the sheet was attached was measured, and the skin temperature change $\Delta T_2$ (° C.) was calculated by the following expression. Incidentally, as a control example, a commercially available cooling gel sheet (gel layer: thickness about 3 mm, fiber layer basis weight: about 96 g/m$^2$, non-woven fabric layer thickness: about 1 mm, hydrous polymer gel moisture content 82.6.7; by mass, no cooling agent blended) was used as Comparative Example 9. The results are shown in FIG. 1.

The skin temperature change $\Delta T_2$(° C.)=(Skin temperature after the sheet is attached)−(Skin temperature before the sheet is attached)

Figure 1:
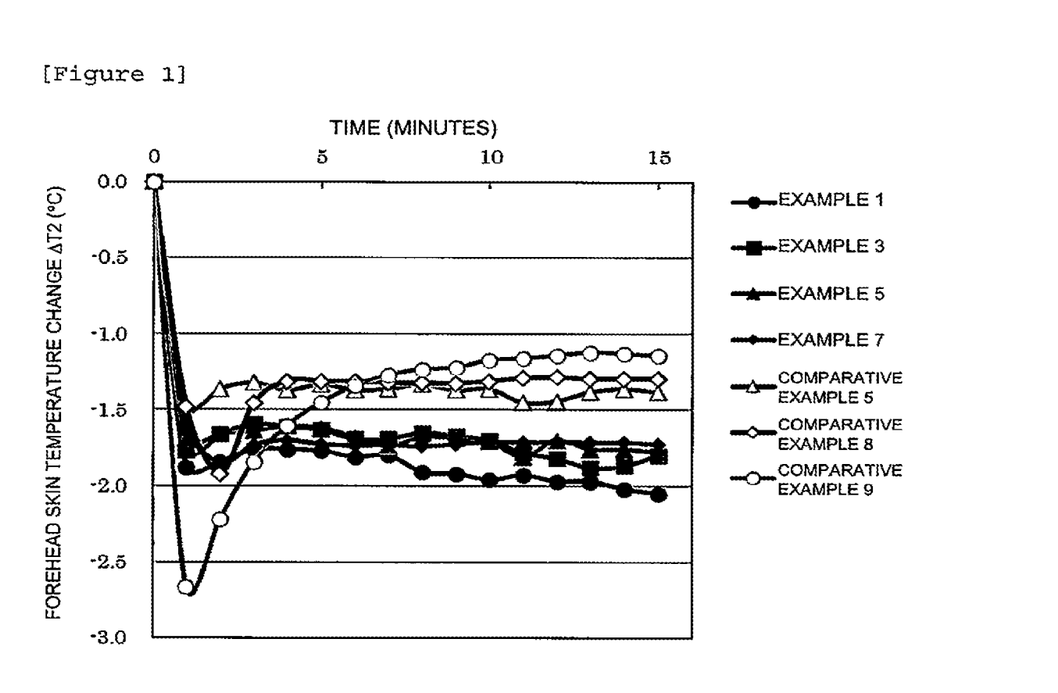
FIG. 1 is a graph showing the skin surface temperature change $\Delta T_2$ (° C.) when sheets of Examples 1, 3, 5, and 7 and Comparative Examples 5, 8, and 9 are each attached to the forehead.
Figure 2:
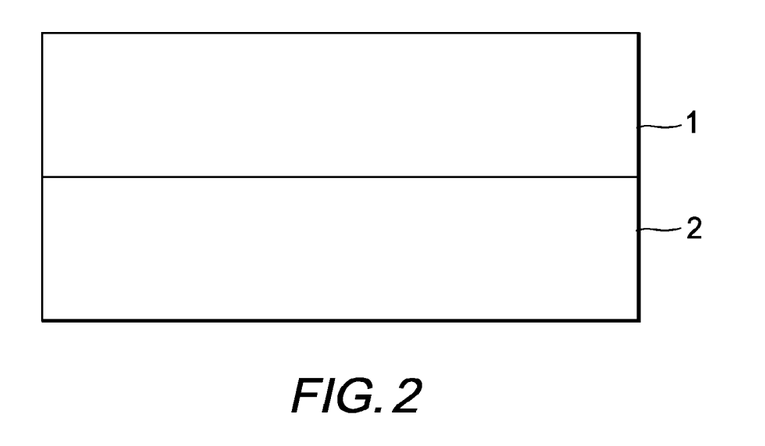
FIG. 2 shows an embodiment of the present adhesive sheet for cooling wherein 1 is the hydrous polymer gel (A) and 2 is the fiber sheet (B).

From the results of FIG. 1, in the adhesive sheets for cooling of Examples 1, 3, 5, and 7, the skin temperature was decreased immediately after the sheet was attached, and thereafter, the skin temperature further persistently was decreased or was not increased. Fifteen minutes after the sheet was attached, decreases in the skin temperature were observed as follows: about 2° C. in Example 1, 1.8° C. in Example 3, 1.8° C. in Example 5, and 1.7° C. in Example 7. In contrast, in Comparative Example 5, a decrease in the skin temperature immediately after the sheet was attached was only 1.5° C., and the skin temperature was not decreased thereafter. Fifteen minutes after the sheet was attached, a decrease of only 1.4° C. in the skin temperature was observed, and it was confirmed that the cooling effect was weak.

Alternatively, in Comparative Example 8, a decrease in the skin temperature of 1.8° C. was observed immediately after the sheet was attached, but the skin temperature was increased thereafter. Fifteen minutes after the sheet was attached, a decrease in the skin temperature of 1.3° C. was observed, and it was confirmed that the cooling effect was weak. Furthermore, in the commercially available cooling gel sheet of Comparative Example 9, a decrease in the skin temperature of 2.6° C. was observed immediately after the sheet was attached, and the skin temperature abruptly was increased thereafter. Fifteen minutes after the sheet was attached, a decrease in the skin temperature of about 1.1° C. was observed, and it was confirmed that the cooling effect was significantly weak. From these results, it has been revealed that, with the adhesive sheet for cooling of the present invention, the cooling effect persists without an increase in the skin temperature of 0.2° C. or more while the sheet is attached to the skin, a high cooling effect is achieved, and a cool feeling persists.

Examples 14 and 15

Adhesive sheets for cooling were prepared in the same manner as Example 3 by using hydrous polymer gels formed in accordance with the formulations shown in Table 2. Incidentally, menthyl lactate (Symrise AG: Frescolat ML) blended in Example 14 or 1-menthol blended in Example 15 was warmed at 50° C. and dissolved in polyethylene glycol (PEG400) followed by mixing in the hydrous polymer gel stock solution for preparation. The hydrous polymer gel of the adhesive sheets for cooling obtained had a pH of 5.3.

Test Example 5: Sensory Evaluation Test

The adhesive sheets for cooling each obtained in Examples 3, 14, and 15 and a commercially available cooling gel sheet in Comparative Example 9 were used to conduct a sensory evaluation test. Specifically, under measurement conditions of a temperature of 29° C. and a humidity of 60% RH, each adhesive sheet for cooling was attached to the forehead for 60 minutes. Five specialized panelists evaluated a cool sensation based on the following criteria, and the average value was taken as the cool feeling score. The results are shown in Table 3.
5: An irritating feeling is sensed
4: A strong cool feeling is sensed
3: A cool feeling is sensed
2: A weak cool feeling is sensed
1: A slight cool feeling is sensed
0: Nothing is sensed

TABLE 3

| | Forehead attaching time (minutes) | | | | | |
|---|---|---|---|---|---|---|
| | 0 | 5 | 10 | 20 | 30 | 45 | 60 |
| Example 3 | 0 | 3.2 | 2.8 | 2.4 | 1.6 | 0.8 | 0.2 |
| Example 14 | 0 | 3.3 | 3.6 | 3.3 | 3.1 | 2.8 | 2.3 |
| Example 15 | 0 | 3.7 | 3.8 | 3.1 | 2.7 | 2.2 | 1.7 |
| Comparative Example 9 | 0 | 1.3 | 0.9 | 0.2 | 0 | 0 | 0 |

From the results of Table 3, in Example 3, it can be seen that an obvious cool feeling persisted until 30 minutes after the sheet was attached. In contrast, in Comparative Example 9, it can be seen that since the skin temperature gradually was increased while the sheet was attached, the sheet might feel lukewarm in a sensation even if the skin temperature was indeed lower than that before the sheet was attached. From these results, it is found that a persistent cooling effect shown in FIG. 1 is considerably associated with the strength and persistency of the cool feeling, and it can be seen that the adhesive sheet for cooling of the present invention has a persistent cool feeling due to its excellent effect of maintaining cooling, which means that the temperature of the skin cooled after the sheet is attached is scarcely increased.

Additionally, it can be seen that Example 14, in which menthyl lactate was blended, or Example 15, in which 1-menthol was blended, as a cooling agent in addition to the components of Example 3, was not only excellent in the cool feeling 30 minutes after the sheet is attached as Example 3, but also provided an excellent cool feeling over an hour or more, having a high persistent effect.

The invention claimed is:

1. An adhesive sheet for cooling comprising a hydrous polymer gel (A) and a fiber sheet (B) laminated thereon:
    the hydrous polymer gel (A) having a moisture content of 655 by mass to 95% by mass, and
    the fiber sheet (B) having a thickness of 0.001 mm to 1 mm, a basis weight of 3 g/m$^2$ to 70 g/m$^2$, and a water absorbency test value of 1 to 16,000 seconds;
    wherein the adhesive sheet has an amount of moisture of 585 g/m$^2$ to 1700 g/m$^2$,
    wherein said adhesive sheet is configured such that a side of said hydrous polymer gel (A), which is opposite to the side in contact with said fiber sheet (B), is in direct contact with skin when in use, and
    said adhesive sheet facilitates transfer of moisture from the hydrous polymer gel to the fiber sheet and transpires moisture from the fiber sheet to thereby persistently decrease the temperature of the area of the skin to which the adhesive sheet is attached.

2. The adhesive sheet for cooling according to claim 1, wherein a value obtained by multiplying the water absorbency test value to the one-third power by a fiber density of the fiber sheet (B) is from $0.25 \times 10^6$ to $2.2 \times 10^6$ seconds$^{1/3}$·g/m$^3$.

3. The adhesive sheet for cooling according to claim 1, wherein a mass ratio of said amount of moisture in said adhesive sheet to fiber in adhesive sheet for cooling is 9 to 320.

4. The adhesive sheet for cooling according to claim 1, wherein an amount of the hydrous polymer gel (A) laminated is 615 g/m$^2$ to 2,600 g/m$^2$.

5. The adhesive sheet for cooling according to claim 1, wherein the fiber sheet (B) is a non-woven fabric sheet.

6. The adhesive sheet for cooling according to claim 1, wherein the fiber sheet (B) comprises a water absorbent fiber.

7. The adhesive sheet for cooling according to claim 6, wherein the water absorbent fiber is one or more members selected from the group consisting of rayon, cellulose, pulp, and polyvinyl alcohol.

8. The adhesive sheet for cooling according to claim 6, wherein a content of the water absorbent fiber in the fiber sheet (B) is 1% by mass to 100% by mass.

9. The adhesive sheet for cooling according to claim 1, wherein the hydrous polymer gel (A) comprises a cooling agent.

10. The adhesive sheet for cooling according to claim 9, wherein a content of the cooling agent in the hydrous polymer gel (A) is 0.0001% by mass to 10% by mass.

11. The adhesive sheet for cooling according to claim 9, wherein the cooling agent is one or more members selected from the group consisting of 1-menthol, menthyl lactate, 1-menthyl glyceryl ether, menthane carbonyl glycine ethyl ester, menthyl ethylamino oxalate, isopulegol, and camphor.

12. A method for cooling, the method comprising:
   contacting a surface of a substrate with said exposed side of said hydrous polymer gel (A) of said adhesive sheet according to claim 1, wherein
   said contacting is carried out for at least 15 minutes upon contacting of the substrate and the adhesive sheet.

13. The method according to claim 12, wherein the substrate is human skin.

\* \* \* \* \*

UNITED STATES PATENT AND TRADEMARK OFFICE
CERTIFICATE OF CORRECTION

| | |
|---|---|
| PATENT NO. | : 11,311,412 B2 |
| APPLICATION NO. | : 15/320413 |
| DATED | : April 26, 2022 |
| INVENTOR(S) | : Yosuke Obata et al. |

It is certified that error appears in the above-identified patent and that said Letters Patent is hereby corrected as shown below:

In the Claims

Column 22, Line 21, Claim 1, "655 by mass", should read --65% by mass--.

Signed and Sealed this
Twentieth Day of September, 2022

Katherine Kelly Vidal
*Director of the United States Patent and Trademark Office*